US011835558B1

United States Patent
Roberts

(10) Patent No.: US 11,835,558 B1
(45) Date of Patent: *Dec. 5, 2023

(54) METHOD FOR CALCULATING DIELECTRIC VERSUS AIR VOID CONTENT RELATIONSHIP FOR ASPHALT CONCRETE USING A SINGLE CALIBRATION MEASUREMENT

(71) Applicant: GEOPHYSICAL SURVEY SYSTEMS, INC., Nashua, NH (US)

(72) Inventor: Roger Roberts, Amesbury, MA (US)

(73) Assignee: GEOPHYSICAL SURVEY SYSTEMS, INC., Nashua, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/990,860

(22) Filed: Nov. 21, 2022

Related U.S. Application Data

(63) Continuation of application No. 17/209,338, filed on Mar. 23, 2021, now Pat. No. 11,513,146.

(60) Provisional application No. 63/140,292, filed on Jan. 22, 2021.

(51) Int. Cl.
  *G01R 27/26* (2006.01)
  *G01N 33/38* (2006.01)
(52) U.S. Cl.
  CPC ....... *G01R 27/2617* (2013.01); *G01N 33/383* (2013.01)

(58) Field of Classification Search
  CPC .......................... G01R 27/2617; G01N 33/383
  See application file for complete search history.

(56) References Cited

U.S. PATENT DOCUMENTS

2005/0150278 A1* 7/2005 Troxler .................. G01N 22/00
                                                             73/78

OTHER PUBLICATIONS

Hashin (Journal of Applied Physics 33, 3125 (1962)). (Year: 2004).*
Leng—Development and validation for in situ asphalt). (Year: 2011).*
Kyle (Toward Core-Free Pavement Compaction Evaluation) (Year: 2019).*

* cited by examiner

*Primary Examiner* — Natalie Huls
*Assistant Examiner* — Sharad Timilsina
(74) *Attorney, Agent, or Firm* — Michael J. Feigin, Esq.; Feigin and Fridman LLC

(57) ABSTRACT

A method for generating a calibration curve of asphalt concrete of a known mix. Initially, a single sample of the known asphalt concrete mix is obtained. The single sample has a known percent voids. A dielectric measurement of the single sample is obtained. Using only the dielectric measurement of the single sample, the sample's known percent voids, and a dielectric of air, a theoretical ideal dielectric for the asphalt concrete mix at 0% voids is computed. A dielectric vs. percent voids calibration curve is generated based on the computed ideal dielectric.

7 Claims, 11 Drawing Sheets

METHOD FOR CALCULATING DIELECTRIC VERSUS AIR VOID CONTENT RELATIONSHIP FOR ASPHALT CONCRETE USING A SINGLE CALIBRATION MEASUREMENT

FIELD OF THE DISCLOSED TECHNOLOGY

The disclosed technology relates generally to methods for computing compaction of asphalt concrete, and, more specifically, to a method to calculate an amount of compaction of asphalt concrete based only on a single calibration measurement.

BACKGROUND OF THE DISCLOSED TECHNOLOGY

There is a need to easily and accurately know the density of a new asphalt road as it is being placed, since controlling its density can double the life of the road. Ground Penetrating Radar (GPR) technology is often used to measure the effective dielectric of asphalt on road surfaces. Knowledge of the effective dielectric of asphalt is useful in calculating the density of the asphalt, or, more accurately, its air void content. Once a calibration curve is created that maps dielectric to air void content, the density can be known simply by measuring the dielectric value at a location on the road.

In the prior art, the relationship between dielectric and air void content is typically determined by obtaining several asphalt samples, usually about 6 inches in diameter and a 2-4 inches thick. By using a few such samples at different air void contents, either drilled from the road (Cores) or created in the lab (Pucks), and by measuring both the dielectric and the air void content of each sample, a curve that maps the two measurements to each other can be calculated. Although useful, this prior art method is laborious, since calibration curves, requiring perhaps 10 cores, are required for hundreds of asphalt mix designs used for paving operations. Furthermore, a mix design selected for a paving project often needs to be adjusted, for example due to changes in the temperature or the ambient moisture (e.g. rain), requiring frequent curve calculations. Daily regeneration of calibration curves is burdensome, since a lab technician must create multiple asphalt samples and measure the densities and dielectrics of such samples each time conditions change.

There is thus a need in the art for an easy method of calibrating the dielectric and air void content of asphalt, preferably using fewer samples and/or regeneration times.

SUMMARY OF THE DISCLOSED TECHNOLOGY

The disclosed technology relates generally to methods for computing compaction of asphalt concrete, and, more specifically, to a method to calculate densities that needs only a single calibration measurement to create a calibration curve. This has implications not only for saving time and money, but more importantly saving lives, since reducing the number of cores needed reduces the hazards associated with collecting them.

This disclosure should be interpreted according to the definitions below. In case of a contradiction between the definitions in this Definitions section and other sections of this disclosure, this section should prevail.

Dielectric—an electromagnetic property that relates to the ability of a material to store energy in the presence of an electric field.

Effective Dielectric—an average dielectric of a micro-inhomogeneous medium, i.e. a medium whose dielectric is not homogeneous on a small scale.

Asphalt—a composite material comprising and having, typically, at least 90% aggregate (i.e. rock fragments) and bitumen, and, in some cases, also including additional materials. Also known as "Pavement" in North America and as "asphalt concrete" in technical papers, these terms are used interchangeably.

Dielectric Mixing Equation—an equation that calculates the effective dielectric of a dielectrically inhomogeneous medium, given volume percentages and dielectrics of constituents in the medium.

Asphalt Air Void Content—The percentage or volume ratio of air in an asphalt sample.

Bitumen—a black viscous mixture of hydrocarbons obtained naturally or as a residue from petroleum distillation. Bitumen is commonly used as a constituent in asphalt concrete. It may also be called tar or binder.

Aggregate—rock and sand constituents typically included in asphalt concrete. Aggregates may be taken from nearby quarries, and as such have highly regional material properties (shape, density, dielectric, porosity etc.).

Air Void—Air trapped inside asphalt concrete. The air void is typically expressed as a percentage of the total volume of asphalt concrete.

Puck—a cylindrical-shaped asphalt sample that is typically compacted to a pre-determined amount using gyratory compactor (and thus typically has a known and predetermined air void percentage).

Percent Compaction—a term used in relation to asphalt paving operations. A sample of asphalt that has one hundred percent compaction contains no air voids. Consequently, percent compaction is calculated from % Voids using the relation: % Compaction=100–% Voids.

Magnetic Permeability—an electromagnetic property that relates the magnetic induction inside a material to the magnetic field intensity.

Mix Design—a particular combination of aggregate, bitumen and possibly other constituents that are mixed together to make asphalt. Different mix designs are customized for the locations where the asphalt is to be used.

In accordance with an embodiment of the disclosed technology, there is provided a novel method for generating a calibration curve of asphalt concrete of a known mix design by measuring only one physical sample. The method involves obtaining a single sample of the known asphalt concrete mix and air void content, and obtaining a dielectric measurement of the single sample. An "ideal dielectric" at a theoretical 0% air void content is then computed using only that sample's measured dielectric value and void content. A dielectric vs. percent compaction calibration curve can then be uniquely determined based only on one measured point and the calculated ideal dielectric value.

In some embodiments, the computing of the ideal dielectric is based on the equation, derived by the inventor for this purpose.

$$\epsilon = \left( \epsilon_s + \frac{f}{\frac{1}{\epsilon_i - \epsilon_s} + \frac{1-f}{3\epsilon_s}} + \epsilon_i + \frac{1-f}{\frac{1}{\epsilon_s - \epsilon_i} + \frac{f}{3\epsilon_i}} \right) / 2$$

where:

∈ is the dielectric measurement of the single puck;

$∈_e$ is the ideal dielectric of the asphalt mix with 0% voids;

$∈_i$ is the dielectric of air; and f is a volume fraction of air in the single puck.

In accordance with some embodiments of the disclosed technology, there is provided a method for identifying a characteristic of a known asphalt mix. A calibration curve for the known asphalt mix is obtained using the method of the disclosed technology described above. A second sample of the asphalt mix is obtained, the second sample having an unknown void percentage, and a second dielectric of the second sample is measured. The second dielectric is compared to the calibration curve, such that when the second dielectric is on the calibration curve, a second air void percentage of the second sample is extracted from the calibration curve.

In some embodiments, when the second dielectric is off the calibration curve, this method can be used to identify the need to decompose and analyze the second sample to understand what changed in the asphalt mix or in the environment surrounding the asphalt mix.

In some embodiments, the method can be used to identify some change in the asphalt mix or in the environment, and to help adjust the asphalt mix to match the calibration curve.

In some other embodiments, the method further includes, in response to identifying some change in the asphalt mix or in the environment, computing an updated calibration curve for the changed asphalt mix or at the changed conditions.

In some embodiments, the method further includes comparing the extracted second air void percentage to an expected air void percentage, and when the extracted second air void percentage is distinct from the expected air void percentage, decomposing and analyzing the second sample to identify a change in the asphalt mix or in an environment surrounding the asphalt mix.

In accordance with some embodiments of the disclosed technology, there is provided a method for calculating a dielectric of an aggregate forming part of an asphalt concrete sample including the aggregate and at least one non-aggregate constituent. The method includes solving the equation of the disclosed technology discussed hereinabove using the ideal dielectric of the asphalt, a known volume percent of the non-aggregate constituents in the asphalt concrete sample, and a dielectric of the non-aggregate constituents.

In accordance with some embodiments of the disclosed technology, there is provided a method for identifying a characteristic of a known asphalt mix. The method includes using a dielectric measurement of a single calibration puck or core of the known asphalt concrete mix and generating a dielectric vs. percent compaction calibration curve for the known asphalt mix. A second sample, which would be a puck or core, of the asphalt mix is obtained and a second dielectric of the second sample is measured. The second sample has an unknown void percentage. The second sample's dielectric is compared to the calibration curve, and when the second sample's dielectric is on the calibration curve, an air void percentage of the second sample is extracted from the calibration curve. When the second sample's dielectric is not on the calibration curve, the second sample is decomposed and analyzed to identify a change to the known asphalt mix, and based on the measured dielectric of the second sample, and the identified change to the known asphalt mix, a revised dielectric vs. percent compaction calibration curve can be generated for the asphalt mix following the change.

In some embodiments, the generating of the calibration curve for the known asphalt mix includes obtaining the single calibration puck or core of the known asphalt concrete mix, the single calibration puck or core having a known void percentage, and obtaining a dielectric measurement of the single calibration puck or core. Using only the dielectric measurement of the single calibration puck or core, components of the known mix, and a dielectric of air, computing an ideal dielectric for the asphalt concrete mix at 0% voids, and generating a dielectric vs. percent compaction calibration curve based only on the dielectric measurement of the single calibration puck or core and on the computed ideal dielectric.

In accordance with some embodiments of the disclosed technology, there is provided a method of projecting an expected dielectric of a known asphalt mix at a specific void percentage. The method includes using a dielectric measurement of a single calibration puck or core of the known asphalt concrete mix, generating a dielectric vs. percent compaction calibration curve for the known asphalt mix, and extracting from the calibration curve for the known asphalt mix the expected dielectric for the known asphalt mix at the specific void percentage.

DETAILED DESCRIPTION OF EMBODIMENTS OF THE DISCLOSED TECHNOLOGY

The disclosed technology provides a method for generating a dielectric to air void curve, or calibration curve, for identifying an amount of compaction of asphalt concrete of a known mix, using a single calibration measurement.

Embodiments of the disclosed technology will become clearer in view of the following description and in view of the drawings.

The method of the disclosed technology is based on a modified form of equations, originally derived to solve a different problem related to the magnetic permeability limits of a mixture of two constituent materials possessing different magnetic permeabilities. The combined magnetic permeability of a mixture can vary depending on how the two constituents are randomly clustered together in the mixture. Certain areas of the mixture may comprise a slightly higher concentration of one constituent, compared to others. The measured magnetic permeability of the mixture thus varies, to some degree, depending on the variations in random clustering.

The Hashin-Shtrikman (HS) equations describe the maximum and minimum magnetic permeability of the mix for each mixing ratio. For example, if two different sands possessing different magnetic permeabilities were to be combined 100 different times in a bucket at even ratios, and mixed with a shovel, the measured magnetic permeability would be within minimum and maximum values calculated using the HS equations.

In embodiments of the disclosed technology, the HS equations have been modified (M-HS equations) to compute the maximum and minimum dielectric values for mixtures comprising or containing constituents having different dielectrics. The inventor has found that the average of the minimum and maximum dielectric values obtained from the M-HS equations describes the relationship of different effective dielectric values and associated air void contents in asphalt exceedingly well, provided that an accurate effective dielectric of the asphalt at "zero percent void content" is substantially known or is known within an acceptable tolerance level.

Asphalt at zero percent void content is known as the Theoretical Maximum Specific Gravity (Gmm), which is the maximum theoretical density of an asphalt mix assuming complete compaction without air voids.

The M-HS is given by:

$$\epsilon = \left( \epsilon_s + \frac{f}{\frac{1}{\epsilon_i - \epsilon_s} + \frac{1-f}{3\epsilon_s}} + \epsilon_i + \frac{1-f}{\frac{1}{\epsilon_s - \epsilon_i} + \frac{f}{3\epsilon_i}} \right) / 2$$

Where:
$\epsilon$ = dielectric of asphalt core or puck;
$\epsilon_e$ = dielectric of corresponding asphalt mix with 0% voids (i.e. GMM dielectric);
$\epsilon_i$ = dielectric of air (1.0); and
f = volume fraction of air (which is % void/100)

Figure 1:
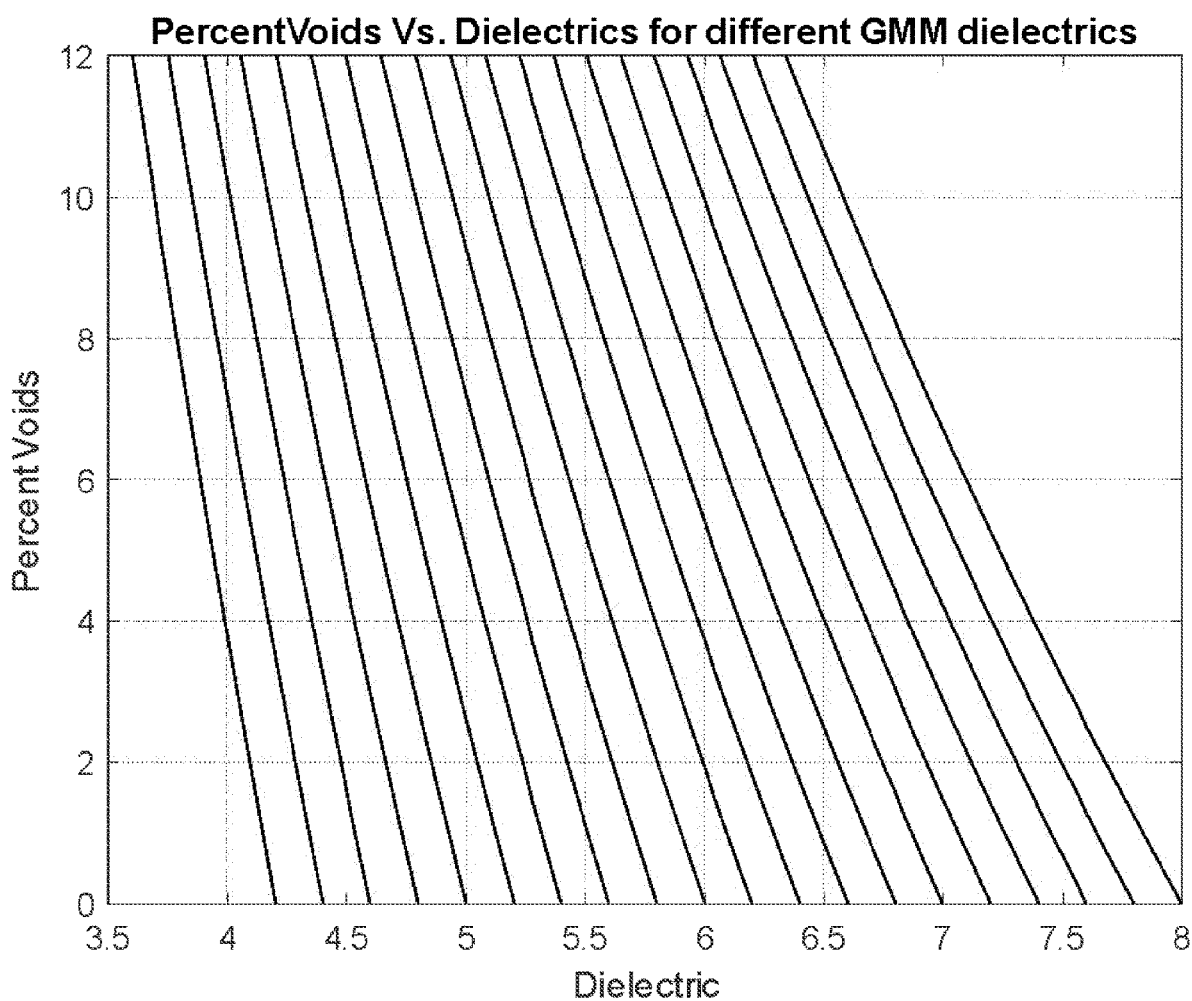
FIG. 1 is a schematic illustration of a plot of dielectric mixing curves using the modified bounds of embodiments of the disclosed technology.

FIG. 1 illustrates a plot of dielectric mixing curves using the average H-S bounds. As seen in FIG. 1, for each dielectric and associated void percent, there is a specific Gmm dielectric. The inventor has discovered that the obtained curves, shown in FIG. 1, are substantially linear, particularly for low dielectrics. This allows the effective dielectric at 0% void, or at Gmm, to be extrapolated or extracted, for example by extending the relatively linear curve or by solving the equation for $\epsilon_e$. In some embodiments of the disclosed technology, the Gmm dielectric can be calculated directly by inserting the known void fraction (f) and associated dielectric ($\epsilon$) of a puck in the modified-HS equation and solving for $\epsilon_e$.

Once the dielectric to void content curve is found, to determine the associated air void content for any single asphalt sample one need only locate any measured dielectric on the calibration curve. Thus, according to the method of the disclosed technology, the calibration curve may be found using a single asphalt puck, enabling easier and more attainable adjustments for daily changes in the asphalt mix or in the ambient conditions.

Figure 2:
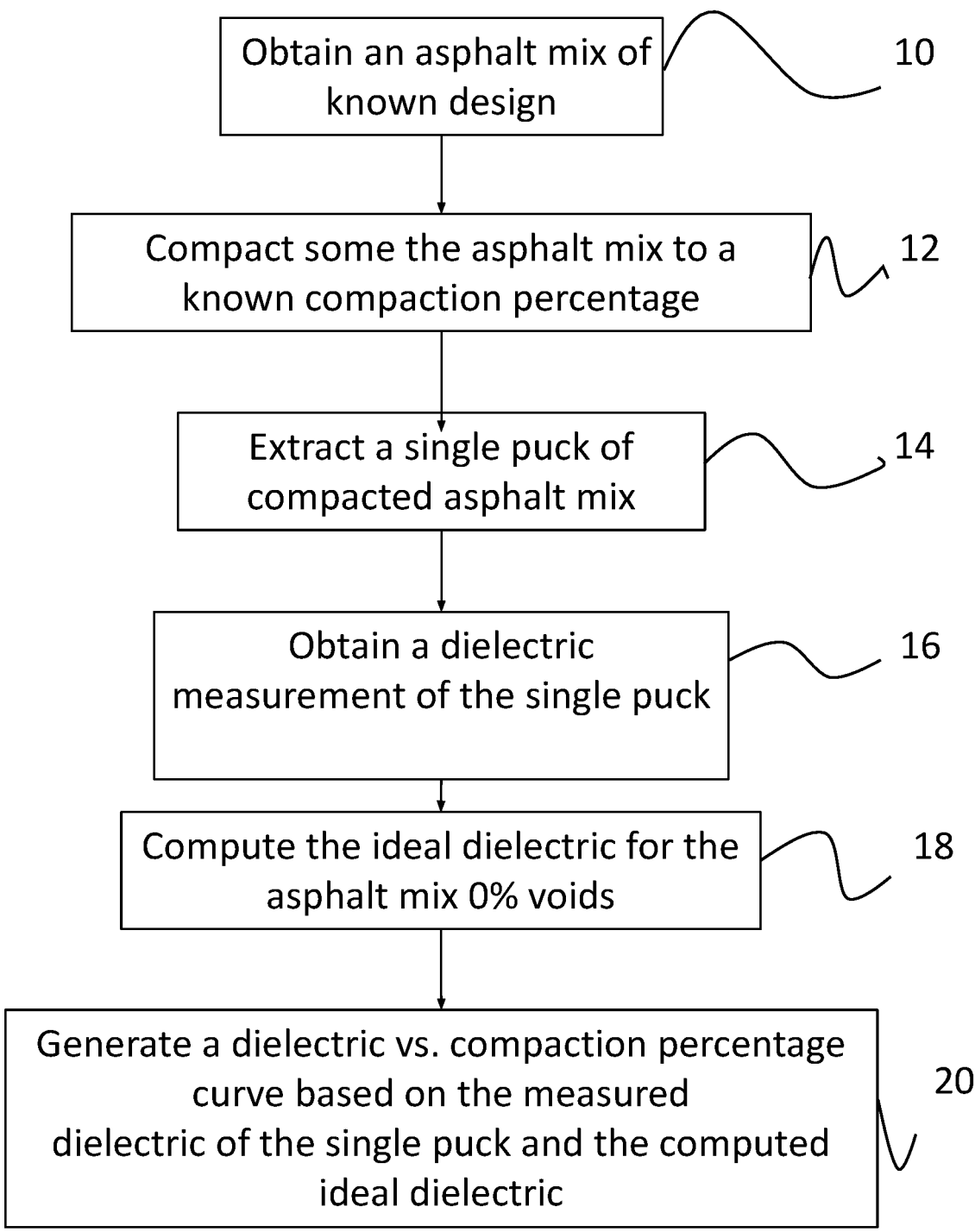
FIG. 2 is a flow chart of an embodiment of a method for generating a calibration curve of asphalt concrete of a known mix, using a single calibration measurement, according to embodiments of the disclosed technology.

Reference is now made to FIG. 2, which is a flow chart of an embodiment of a method for generating a calibration curve of asphalt concrete of a known mix, using a single calibration measurement, according to embodiments of the disclosed technology.

At step 10, a known asphalt mix design is obtained, with known proportions of known constituent materials. A portion of the asphalt mix is then compacted to generate a puck of known compaction percentage at step 12. A dielectric measurement of the asphalt mix with the known compaction percentage is obtained at step 14 from the puck of step 12. The first dielectric measurement, extracted at step 14, is a control or baseline measurement for the asphalt mix.

At step 16, the ideal dielectric for the asphalt mix at 100% compaction, or the Gmm dielectric for the asphalt mix, is determined, for example by solving the M-HS equations discussed hereinabove to obtain a value of the Gmm dielectric. A dielectric vs. compaction percentage curve for the asphalt mix is generated, or determined, at step 18, based on the measured dielectric for the obtained puck and the computed Gmm dielectric for the asphalt mix. As discussed hereinbelow, the curve generated in step 18 may function as a calibration curve, for identifying the compaction level of any puck or sample of the asphalt mix.

Figure 3:
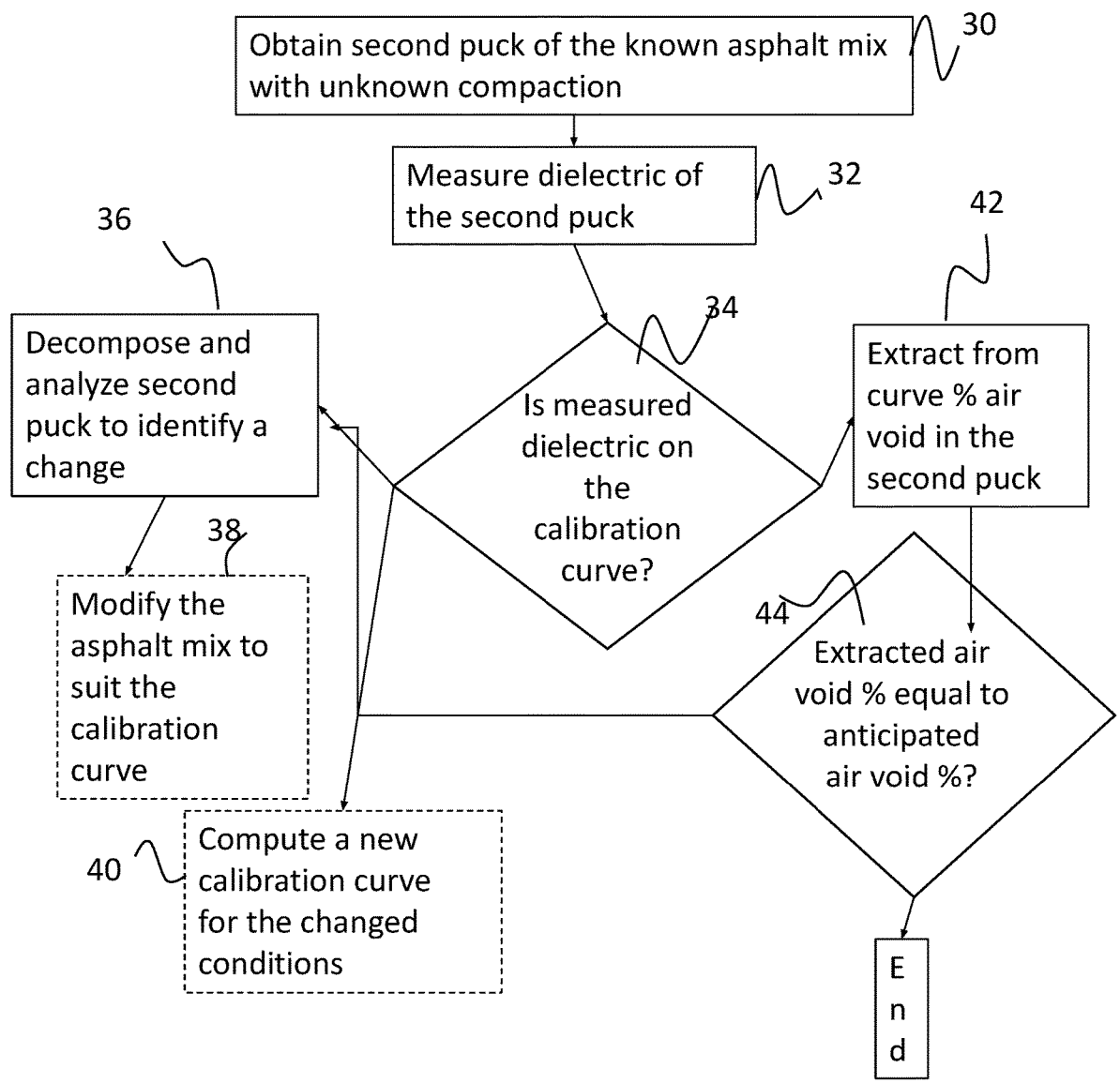
FIG. 3 is a flow chart of an embodiment of a method for using a calibration curve, such as the one generated using the method of FIG. 2, for identifying a characteristic of an asphalt mix, according to embodiments of the disclosed technology.

Reference is now made to FIG. 3, which is a flow chart of an embodiment of a method for using a calibration curve, such as the one generated using the method of FIG. 2, for identifying a characteristic of an asphalt mix, according to embodiments of the disclosed technology. For the purpose of the description of FIG. 3, it is assumed that the calibration curve for the asphalt mix is already known.

At step 30, a second puck of the known asphalt mix, having an unknown compaction percentage, is obtained. For example, the second puck may be obtained by compacting asphalt obtained from a truck delivering asphalt to a paving job location. A second dielectric value corresponding to the second puck is measured at step 32. At step 34, the second measured dielectric is compared to the calibration curve.

If it is determined, at step 34, that the measured dielectric is outside of the calibration curve (or sufficiently outside of the calibration curve to be considered more than a tolerance or measurement error), this may be indicative of a change in the asphalt mix or in the environment. For example, the dielectric may be off of the expected curve if there has been an unknown change to the mix design (e.g. more bitumen was added to the mix on a very cold day to make it more workable), if there has been a change to the moisture level in the mix (e.g. if the mix had been rained upon), or if there has been a change to the aggregate—to the sand or rock mineral content in the mix.

In such embodiments, at step 36, the second puck may be decomposed and analyzed, in order to determine what has changed about the asphalt mix or about the environment. In some embodiments, at step 38, the asphalt mix is modified to compensate for changes identified during the analysis of step 36, so that the modified asphalt mix once again suits the computed curve. In some other embodiments, at step 40, a new calibration curve is computed for the asphalt mix, following the change identified at step 36, for example using the method of FIG. 2. The new calibration curve may then be used for all required computations using the asphalt mix following the change it had undergone.

If it is determined, at step 34, that the measured dielectric is on the calibration curve, the percentage of air voids in the second puck may be extracted from the curve at step 42. In some embodiments, the extracted percentage of air voids in the second puck is compared to an anticipated (theoretical) air void percentage value, at step 44. If the extracted percentage of air voids in the second puck matches the anticipated air void percentage, the method terminates, as the air void percentage of the second puck is known. Otherwise, if extracted percentage of air voids in the second puck does not match the anticipated air void percentage value, the flow may proceed to step 36, for analysis of the second puck in order to understand why the mismatch has occurred.

In some embodiments, the M-HS equations described hereinabove may further be used to calculate the dielectric of one main component of an asphalt sample, assuming the dielectric and volume percentage of the other main component are known. For example, one can calculate the dielectric of the aggregate, if the dielectric and volume percentage of the bitumen are known. This yields key information to pavement engineers because anomalous aggregate dielectrics alert the operator to changes in the aggregate composition and/or in the moisture content. For example, if the dielectric of the aggregate when it is dry is known, an excessively high calculated aggregate dielectric from an asphalt sample infers the presence of moisture in the aggregate.

Figure 4:
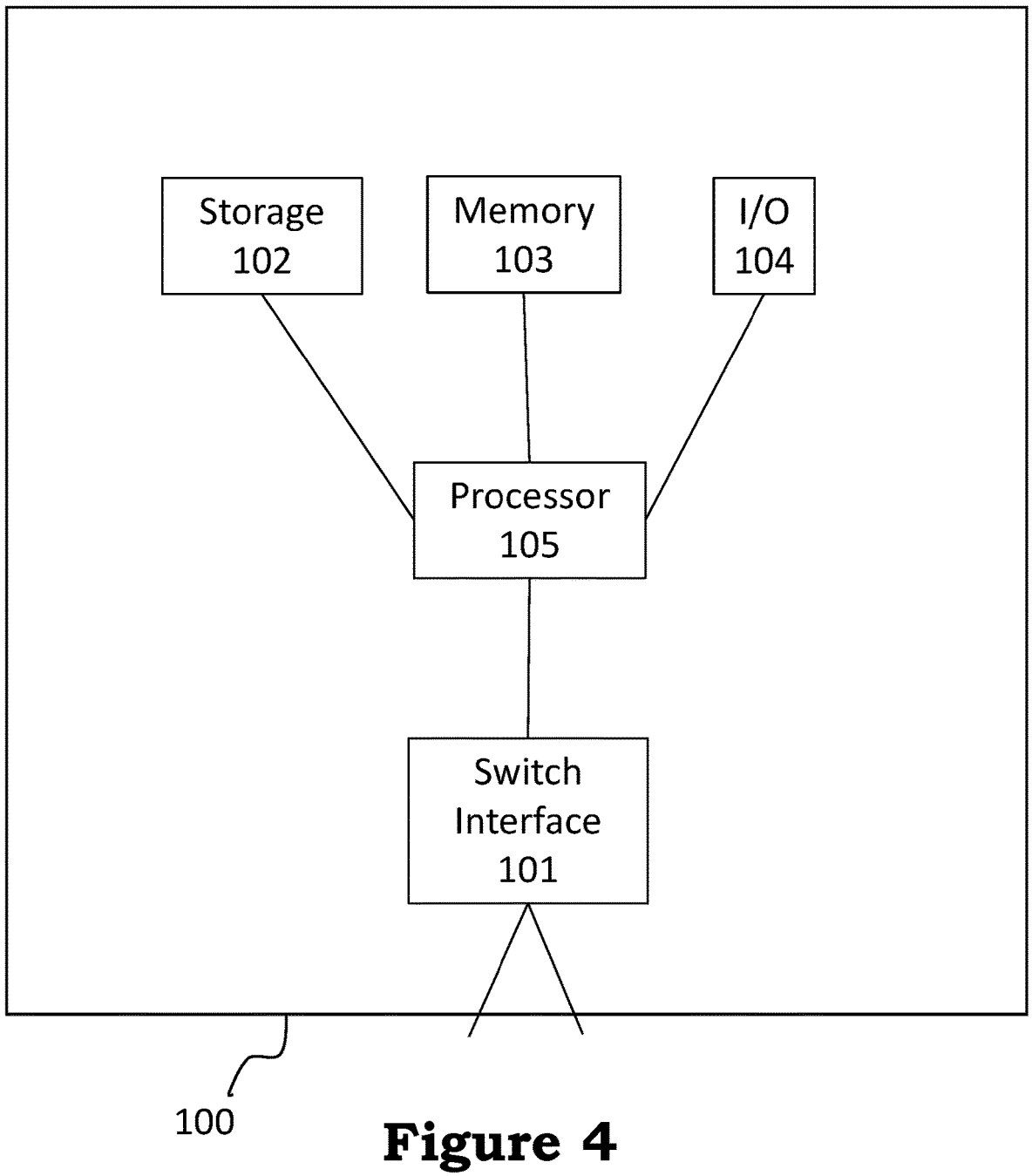
FIG. 4 is a high-level block diagram showing devices on which embodiments of the disclosed technology may be carried out.

FIG. 4 shows a high-level block diagram of a device that may be used to carry out the disclosed technology. Device 100 comprises a processor 105 that controls the overall operation of the computer by executing the device's program instructions which define such operation. The device's program instructions may be stored in a storage device 102 (e.g., magnetic disk, data-base) and loaded into memory 103, when execution of the console's program instructions is desired. Thus, the device's operation will be defined by the device's program instructions stored in memory 103 and/or storage 102, and the console will be controlled by processor 105 executing the console's program instructions. A device 100 also includes one, or a plurality of, input network interfaces for communicating with other devices via a network (e.g., the Internet). The device 100 further includes an electrical input interface. A device 100 also includes one or more output network interfaces 101 for communicating with other devices. Device 100 also includes input/output 104, representing devices which allow for user interaction with a computer (e.g., display, keyboard, mouse, speakers, buttons, etc.). One skilled in the art will recognize that an implementation of an actual device will contain other components as well, and that FIG. 4 is a high-level representation of some of the components of such a device, for illustrative purposes. It should also be understood by one skilled in the art that the method and devices depicted in FIGS. 1 through 3 may be implemented on a device such as is shown in FIG. 4.

EXAMPLES

Reference is now made to the following examples, which, together with the above description, illustrate the invention in a non-limiting fashion. Specifically, the examples provided herein demonstrate that the method of generating a calibration curve as described hereinabove with respect to FIG. 2, is functionally equivalent to prior art methods of generating a calibration curve using analysis requiring many pucks of an asphalt mix.

Example 1

Figure 5A:
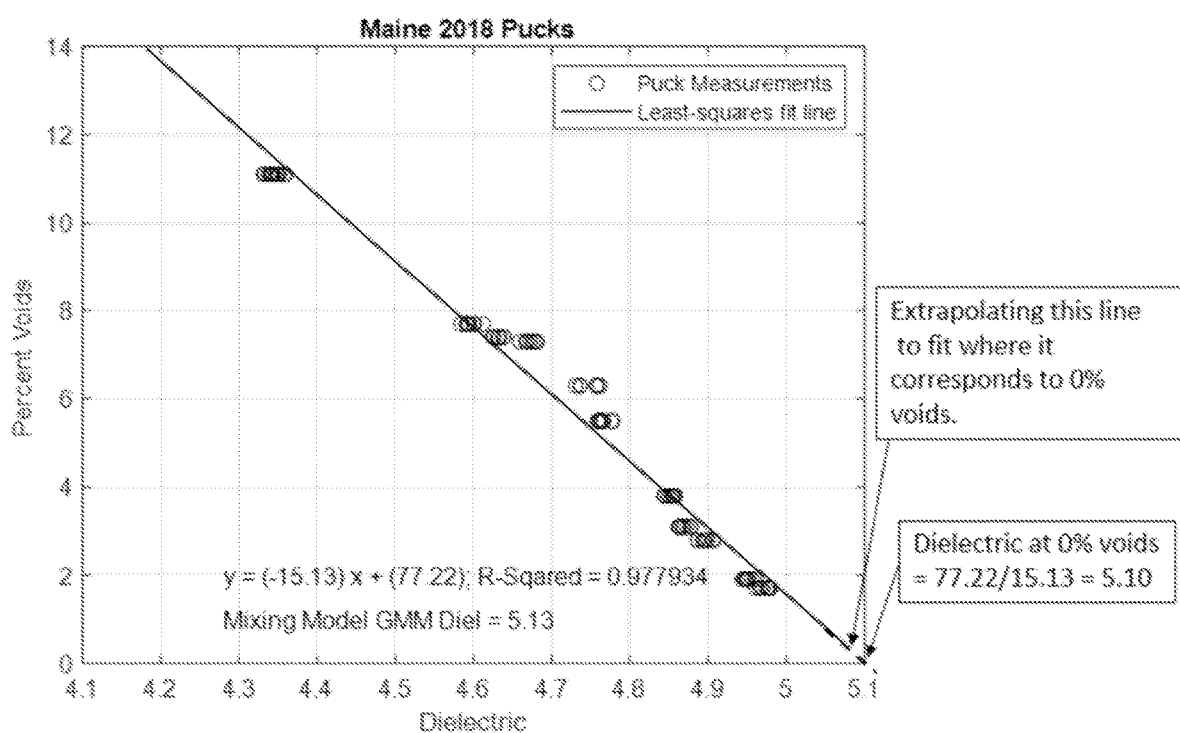
FIGS. 5A, 5B, and 5C are graphs comparing characteristics of implementation of the method of FIG. 2 according to embodiments of the disclosed technology and prior art methods, using a first dataset generated from sample pucks.

A dataset of 12 pucks obtained from Maine was used to generate a first calibration curve, shown in FIG. 5A. The calibration curve of FIG. 5A, which was generated using a least-squares fit line in accordance with prior art methods, plots the measured dielectric vs. the known void percentage for each puck in the dataset, and a linear approximation of the locations of the pucks is assumed to be the calibration curve. The linear approximation was then extended, as indicated by a dashed line in FIG. 5A, to extrapolate the corresponding dielectric value for a mix having 0% voids, or the Gmm, which was equal to 5.10.

Figure 5B:
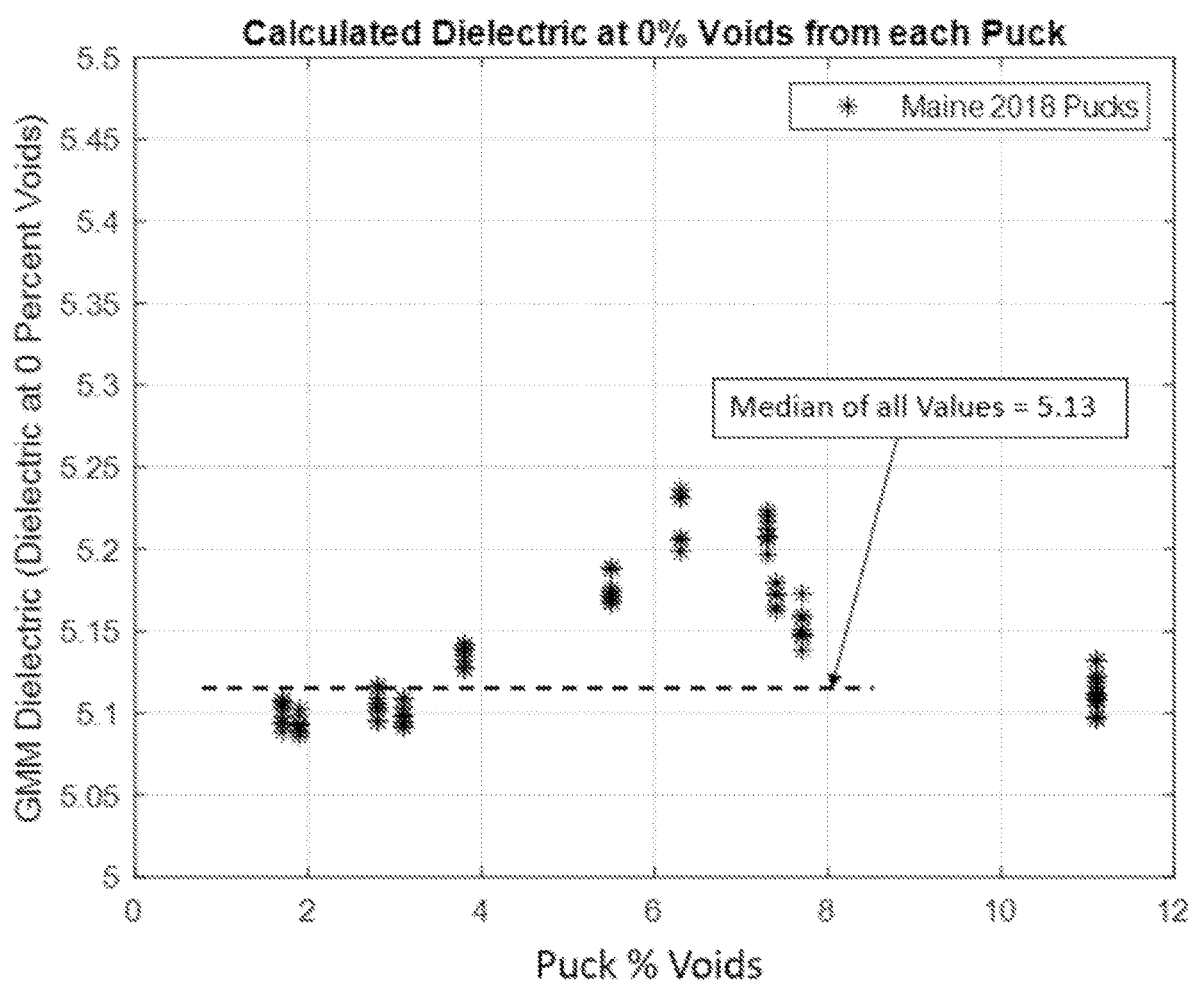

For each of the 12 pucks in the Maine dataset, the dielectric at Gmm was computed using the method of the disclosed technology, as described herein with respect to FIG. 2. FIG. 5B plots the dielectric at Gmm vs. measured % voids, as computed based on each of the pucks. The median Gmm value for all the pucks, indicated by a horizontal line in the graph of FIG. 5B, is at a dielectric value of 5.13—within 0.03 of the value obtained in FIG. 5A using a least-squares fit curve for the dielectrics and void percentage of each puck.

Figure 5C:
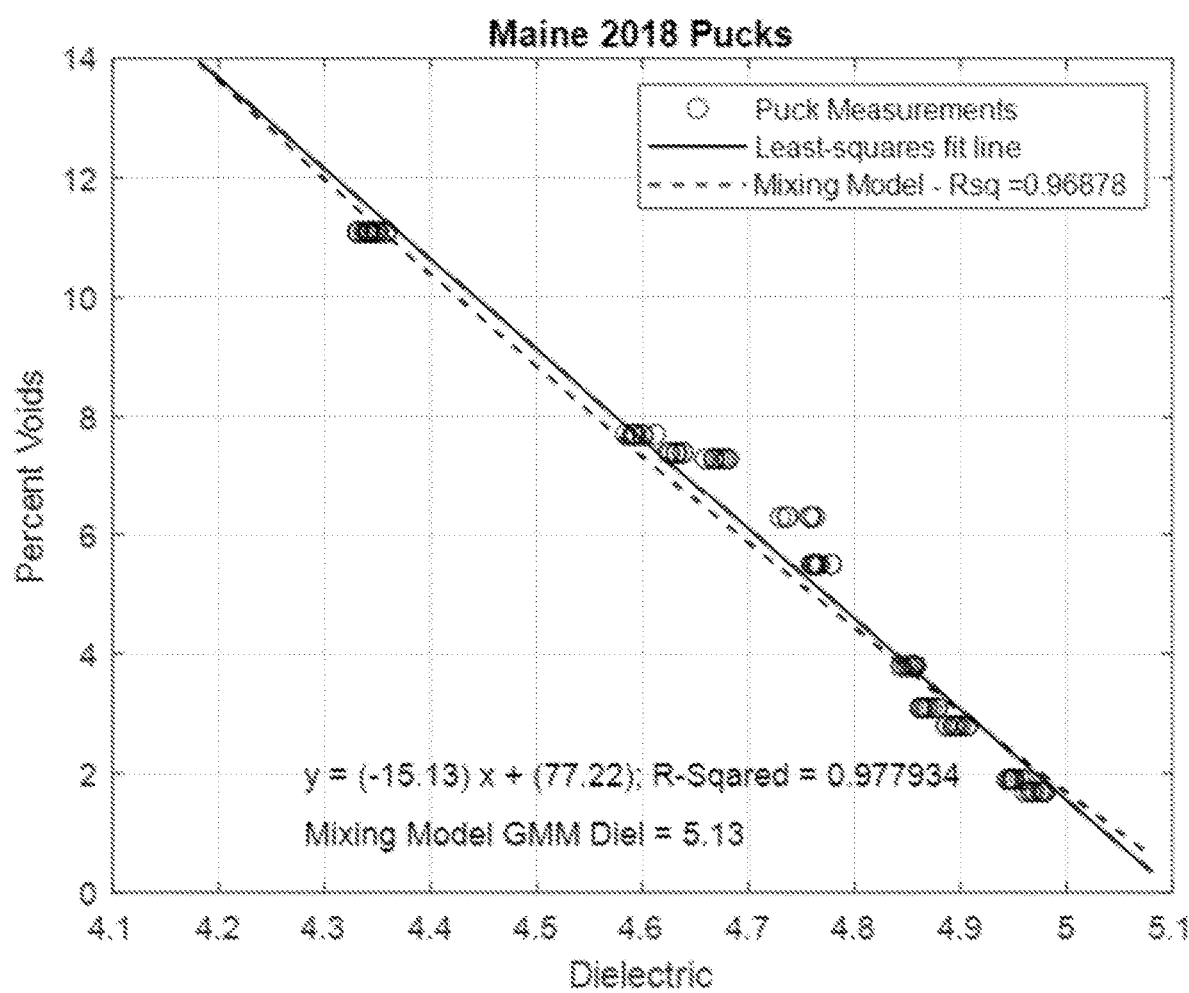

The median of individual Gmm dielectrics calculated in FIG. 5B was used to generate a calibration curve for the mix, based on the mixing model described hereinabove, and specifically based on the modified H-S equations. As seen in FIG. 5C, the curve computed using prior art methods, based on measurement of multiple pucks, and the curve computed using the method of the present invention, are very similar to each other.

Example 2

Figure 6:
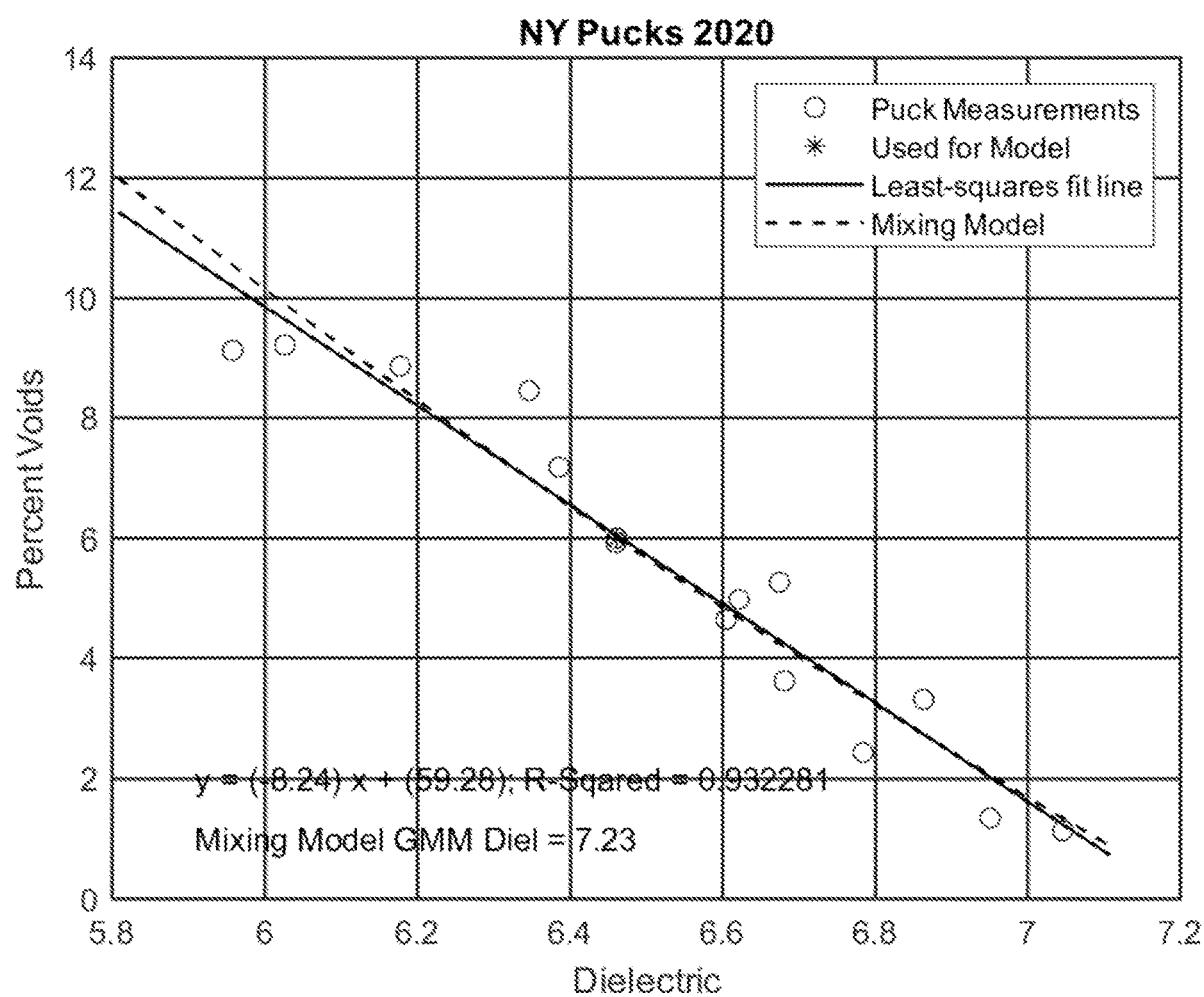
FIG. 6 is a graph comparing characteristics of implementation of the method of FIG. 2 according to embodiments of the disclosed technology and prior art methods, using a second dataset generated from sample pucks.

A dataset of pucks obtained in NY in 2020 was used to generate two calibration curves, shown in FIG. 6. The first calibration curve of FIG. 6, is indicated by a solid line and was generated using a least-squares fit line in accordance with prior art methods, plots the measured dielectric vs. the known void percentage for each puck in the dataset, and a linear approximation of the locations of the puck measurements is assumed to be the calibration curve.

A second calibration curve for the mix, indicated by a dashed line in FIG. 6, was generated using only the measured dielectric and known % voids of the of the puck having 6% voids, based on the mixing model described hereinabove, and specifically based on the M-HS equations. As seen in FIG. 6, the curve computed using prior art methods, based on measurement of multiple pucks, and the curve computed using the method of the present invention, are very similar to each other.

Example 3

Figure 7:
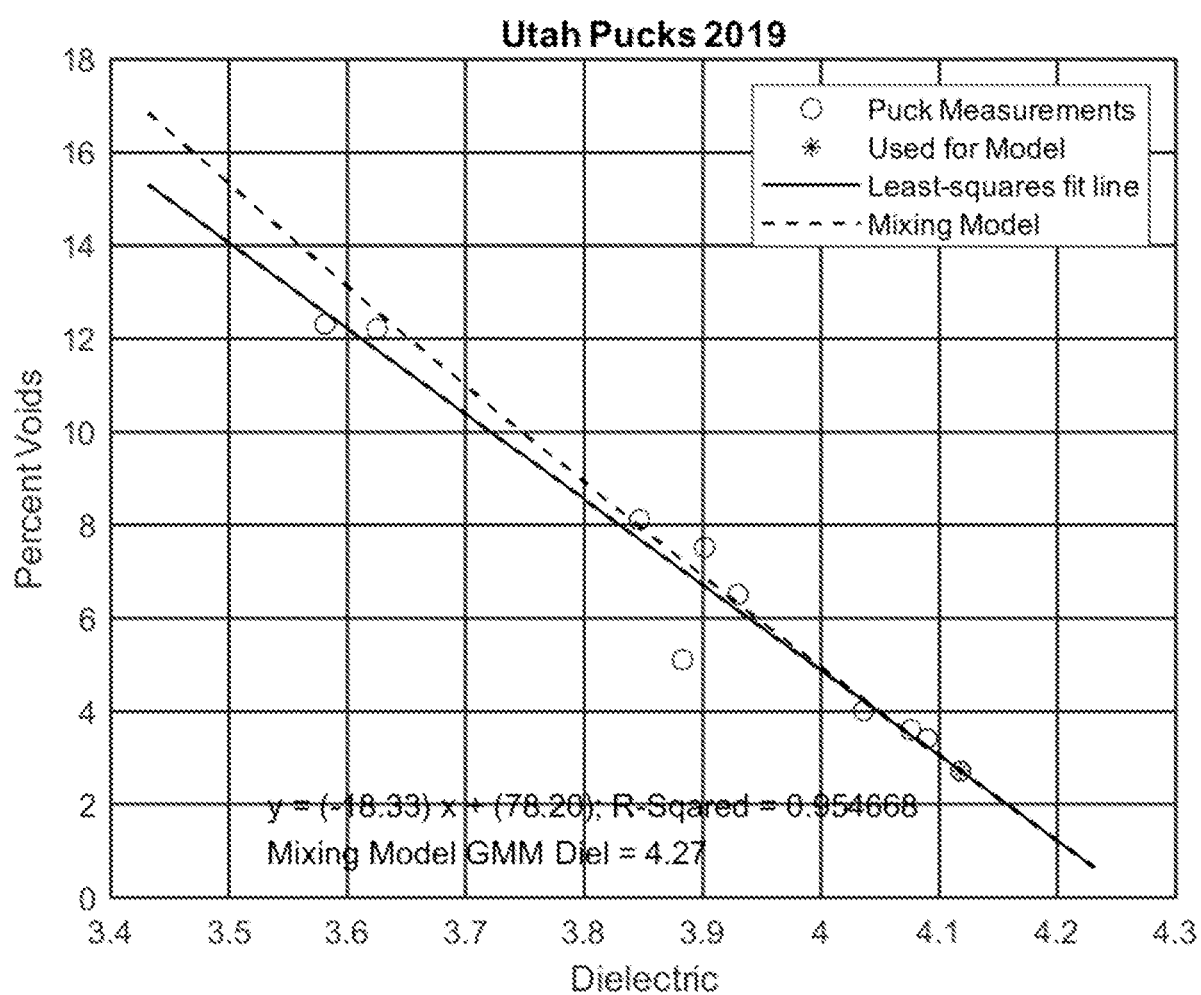
FIG. 7 graph comparing characteristics of implementation of the method of FIG. 2 according to embodiments of the disclosed technology and prior art methods, using a third dataset generated from sample pucks.

A dataset of pucks obtained from Utah in 2019 was used to generate two calibration curves, shown in FIG. 7. The first calibration curve of FIG. 7, is indicated by a solid line and was generated using a least-squares fit line in accordance with prior art methods, plots the measured dielectric vs. the known void percentage for each puck in the dataset, and a linear approximation of the locations of the puck measurements is assumed to be the calibration curve.

A second calibration curve for the mix, indicated by a dashed line in FIG. 7, was generated using only the measured dielectric and known % voids of the of the puck having 2.5% voids, based on the mixing model described hereinabove, and specifically based on the M-HS equations. As seen in FIG. 7, the curve computed using prior art methods, based on measurement of multiple pucks, and the curve computed using the method of the present invention, are very similar to each other, particularly for lower void percentages.

Example 4

Figure 8:
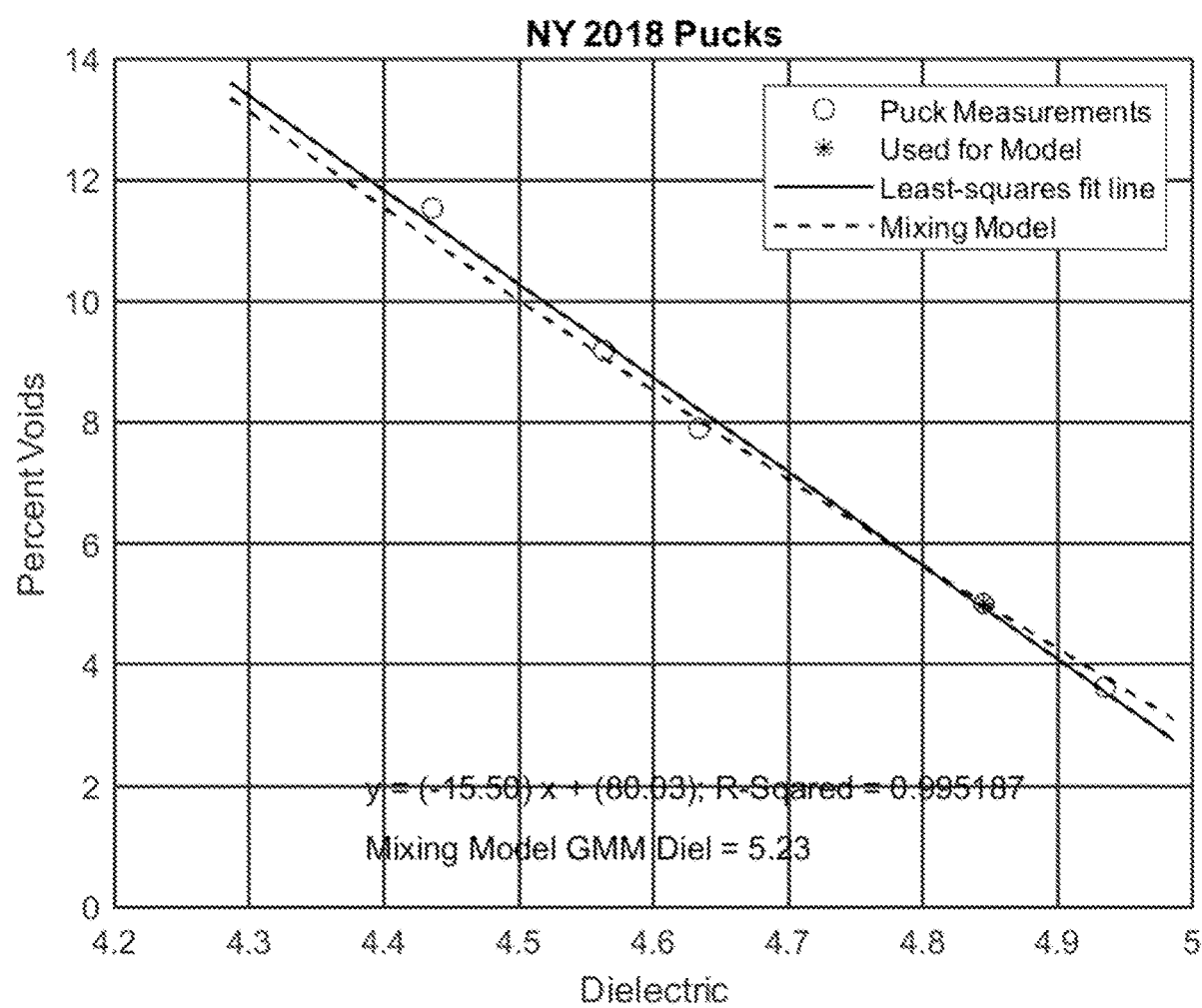
FIG. 8 is a graph comparing characteristics of implementation of the method of FIG. 2 according to embodiments of the disclosed technology and prior art methods, using a fourth dataset generated from sample pucks.

A dataset of pucks obtained in 2018 from New York was used to generate two calibration curves, shown in FIG. 8. The first calibration curve was generated using a least-squares fit line in accordance with prior art methods, plots the measured dielectric vs. the known void percentage for each puck in the dataset, and a linear approximation of the locations of the puck measurements is assumed to be the calibration curve.

A second calibration curve for the mix was generated using only the measured dielectric and known % voids of the puck having 5% voids, based on the mixing model described hereinabove, and specifically based on the M-HS equations. As seen in FIG. 8, the curve computed using prior art methods, based on measurement of multiple pucks, and the curve computed using the method of the present invention, are very similar to each other.

Example 5

Figure 9:
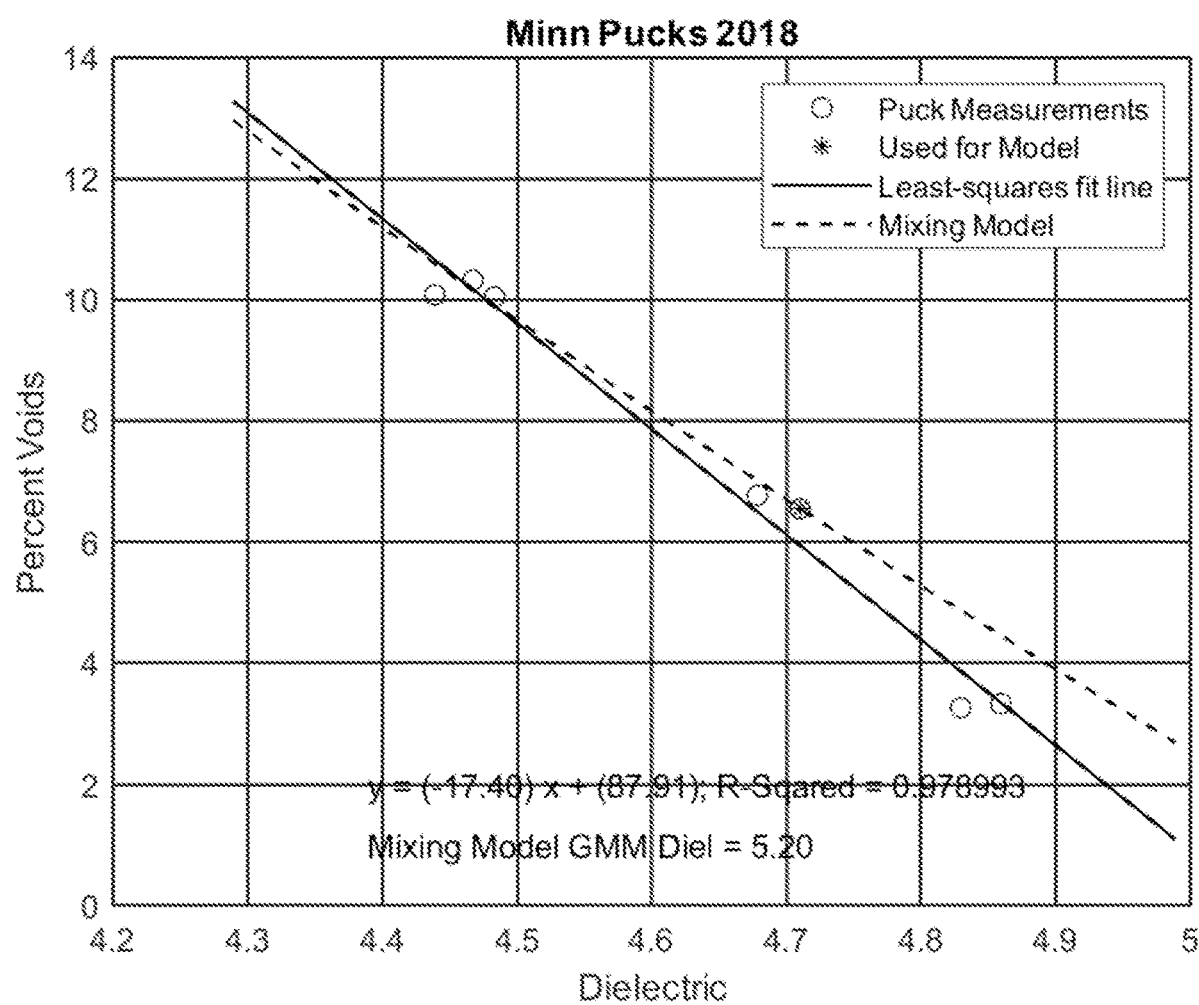
FIG. 9 is a graph comparing characteristics of implementation of the method of FIG. 2 according to embodiments of the disclosed technology and prior art methods, using a fifth dataset generated from sample pucks.

A dataset of pucks obtained in 2018 from Minnesota was used to generate two calibration curves, shown in FIG. 9. The first calibration curve of FIG. 9 was generated using a least-squares fit line in accordance with prior art methods, plots the measured dielectric vs. the known void percentage for each puck in the dataset, and a linear approximation of the locations of the puck measurements is assumed to be the calibration curve.

A second calibration curve for the mix was generated using only the measured dielectric and known % voids of the puck possessing 6.5% voids, based on the mixing model described hereinabove, and specifically based on the M-HS equations. As seen in FIG. 9, the curve computed using prior art methods, based on measurement of multiple pucks, and the curve computed using the method of the present invention, are very similar to each other.

Example 6

In order to determine the accuracy of the method of the disclosed technology relative to the method of the prior art for predicting the dielectric at a specific void percentage, not explicitly measured in a puck, the five datasets of pucks discussed hereinabove with respect to Examples 1-5 were compared to each other. For each of the datasets, the expected dielectric for a puck having 8% void (or 92% compaction) was extracted from the graph generated using the near fit squares of the prior art, and from the graph generated using the mixing model and the method of the disclose technology. The 92% compaction value is of particularly important because paving contractor bonuses and/ or penalties often depend on the percentage of asphalt compacted above and/or below this threshold level. The results are shown in Table 1:

| Puck Dataset | Linear Fit Dielectric for 8% void | Mixing Model Dielectric for 8% void | Absolute difference |
| --- | --- | --- | --- |
| Maine 2018 | 4.575 | 4.611 | 0.037 |
| NY 2020 | 6.226 | 6.232 | 0.006 |
| Utah 2019 | 3.831 | 3.845 | 0.014 |
| NY 2018 | 4.648 | 4.635 | 0.013 |
| Minnesota 2018 | 4.591 | 4.611 | 0.020 |

As clearly seen from Table 1, in all the puck datasets, the dielectric for 8% void, projected based on the prior art methods and projected based on the method of the disclosed technology, are within 0.04 of one another, indicating that the method of the disclosed technology is equivalent, in terms of quality, to the prior art methods, while being much simpler and much less time consuming, and overcoming the limitations discussed in the background section hereinabove.

For purposes of this disclosure, the term "substantially" is defined as "at least 95% of" the term which it modifies.

Any device or aspect of the technology can "comprise" or "consist of" the item it modifies, whether explicitly written as such or otherwise.

When the term "or" is used, it creates a group which has within either term being connected by the conjunction as well as both terms being connected by the conjunction.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods and apparatuses described hereinabove are also contemplated and within the scope of the invention.

The invention claimed is:

1. A method for generating and using a calibration curve of asphalt concrete of a known mix, the method comprising:

obtaining a single sample of the asphalt concrete mix, the single sample being formed as a puck or core extracted from paved asphalt and having a known percent voids;

obtaining a dielectric measurement of the single sample;

using only the dielectric measurement of the single sample, computing an ideal dielectric for the asphalt concrete mix at 0% voids;

generating a dielectric vs. percent voids calibration curve based only on the dielectric measurement of the single sample and on the computed ideal dielectric, obtaining a second sample of the asphalt mix, the second sample having an unknown void percentage;

measuring a second dielectric of the second sample;

comparing the second dielectric to the calibration curve; and when the second dielectric is off the calibration curve, decomposing and analyzing the second sample to identify a change in the asphalt mix or in an environment surrounding the asphalt mix.

2. The method of claim 1, wherein the computing of the ideal dielectric is based on the equation $$\epsilon = \left( \epsilon_s + \frac{f}{\frac{1}{\epsilon_i - \epsilon_s} + \frac{1-f}{3\epsilon_s}} + \epsilon_i + \frac{1-f}{\frac{1}{\epsilon_s - \epsilon_i} + \frac{f}{3\epsilon_i}} \right) / 2$$

where:

$\epsilon$ is the dielectric measurement of the single sample;

$\epsilon_e$ is the ideal dielectric of the asphalt mix with 0% voids;

$\epsilon_i$ is the dielectric of air; and f is a volume fraction of air in the single sample.

3. The method of claim 1, further comprising:

when the second dielectric is on the calibration curve, extracting from the calibration curve a second air void percentage of the second sample.

4. The method of claim 1, further comprising, in response to identifying the change in the asphalt mix or in the environment, modifying the asphalt mix to match the calibration curve.

5. The method of claim 1, further comprising, in response to identifying the change in the asphalt mix or in the environment, computing an updated calibration curve for the changed asphalt mix or at the changed conditions.

6. The method of claim 3, further comprising:

comparing the extracted second air void percentage to an expected air void percentage; and when the extracted second air void percentage is distinct from the expected air void percentage, decomposing an analyzing the second sample to identify a change in the asphalt mix or in an environment surrounding the asphalt mix.

7. The method of claim 1, wherein the ideal dielectric of a mix is generated from the average or median of ideal dielectrics calculated individually from two or more asphalt samples.

\* \* \* \* \*